United States Patent [19]

Labriola, II

[11] Patent Number: 4,912,976
[45] Date of Patent: Apr. 3, 1990

[54] LIQUID LEVEL SENSING APPARATUS

[75] Inventor: Donald P. Labriola, II, La Verne, Calif.

[73] Assignee: Beckman Instruments, Inc., Fullerton, Calif.

[21] Appl. No.: 67,183

[22] Filed: Jun. 26, 1987

[51] Int. Cl.[4] .......................... B65B 1/04; G01R 27/26
[52] U.S. Cl. .................................... 73/290 R; 141/95; 324/675; 331/65; 340/620
[58] Field of Search .................... 73/290 R, 304 C; 324/61 QS; 331/65; 141/95, 83; 340/620

[56] References Cited

U.S. PATENT DOCUMENTS

| | | | |
|---|---|---|---|
| 2,657,579 | 11/1953 | Milson | 73/304 C |
| 2,792,566 | 5/1957 | Shanhouse et al. | 340/244 |
| 3,277,711 | 10/1966 | Roberge | 73/304 C |
| 3,321,971 | 5/1967 | Llewellyn et al. | 73/304 |
| 3,596,673 | 8/1971 | Laucourmet et al. | 137/209 |
| 3,635,094 | 1/1972 | Oberli | 73/423 A |
| 3,641,544 | 2/1972 | Radin | 73/304 R |
| 3,687,632 | 9/1972 | Natelson | 23/259 |
| 3,694,804 | 9/1972 | Hill | 340/59 |
| 3,793,585 | 2/1974 | Wilska | 324/61 QS |
| 3,807,231 | 4/1974 | Spaw | 73/290 R |
| 3,821,900 | 7/1974 | Preikschat | 73/304 C |
| 4,099,167 | 7/1978 | Pomerantz et al. | 340/620 |
| 4,165,641 | 8/1979 | Pomerantz | 73/290 R |
| 4,170,135 | 10/1979 | Booman et al. | 73/290 R |
| 4,182,176 | 1/1980 | Playfoot et al. | 73/304 R X |
| 4,276,258 | 6/1981 | Ginsberg et al. | 422/64 |
| 4,326,851 | 4/1982 | Bello et al. | 23/230 |
| 4,389,900 | 6/1983 | Gutierrez | 73/861.42 |
| 4,423,628 | 1/1984 | Richter | 73/290 R |
| 4,482,891 | 11/1984 | Spencer | 340/620 |
| 4,495,807 | 1/1985 | Field et al. | 73/290 R |
| 4,502,126 | 2/1985 | Mizoguchi | 364/509 |
| 4,543,823 | 10/1985 | Nagy et al. | 73/304 C |
| 4,615,351 | 10/1986 | Schliefer et al. | 137/2 |
| 4,647,854 | 3/1987 | Yamada et al. | 73/290 R |
| 4,736,638 | 4/1988 | Okawa et al. | 73/304 C X |

FOREIGN PATENT DOCUMENTS

| | | |
|---|---|---|
| 2055590 | 3/1972 | Fed. Rep. of Germany . |
| 58-180916 | 10/1983 | Japan . |
| 663643 | 12/1951 | United Kingdom . |
| 1287148 | 8/1972 | United Kingdom .................. 73/244 |
| 1586641 | 3/1981 | United Kingdom . |

OTHER PUBLICATIONS

European Patent Publication; No. 0101580–Berwind Corporation, published 02/29/84.

Primary Examiner—Daniel M. Yasich
Attorney, Agent, or Firm—William H. May; Arnold Grant; Gary T. Hampson

[57] ABSTRACT

A liquid level sensing system comprising a probe and a reactive element carried by the probe. The reactive element forms a portion of a tuned circuit in a voltage-controlled oscillator. The output of the voltage-controlled oscillator is compared to a fixed frequency reference signal and a frequency/phase detector generates a signal indicative of any difference. The frequency/phase detector output is applied to the voltage-controlled oscillator to maintain the output frequency of the oscillator at the frequency of the reference signal. The output of the frequency/phase detector is also differentiated to develop a pulse when the frequency/phase detector output signal varies rapidly, indicating initial contact between the probe and the surface of a liquid held within a container.

23 Claims, 2 Drawing Sheets

LIQUID LEVEL SENSING APPARATUS

FIELD OF THE INVENTION

The present invention relates generally to the field of liquid handling devices and apparatus and more particularly to an improved liquid level sensing apparatus.

BACKGROUND OF THE INVENTION

Various techniques are known in the art for detecting the level of liquid in a container. Some techniques are based on detecting the initial contact between a sensing element and the surface of the liquid. The initial contact may result from the sensing element moving toward the liquid surface or may occur where the sensing element is fixed with respect to the container and the liquid level rises to meet the element. In either instance, a device connected to the sensing element detects a change in some parameter sensed by the probe which indicates contact between the sensing element and the liquid surface Other techniques use a sensing element that is fixed within the container and which extends over an anticipated range of liquid levels. As the liquid level changes within the container, a device connected to the sensing element measures a parameter which changes with the liquid level to provide a continuous indication of liquid level.

With either type of liquid level detecting technique, it is known to use capacitance as the parameter that is sensed by the sensing element. Several problems exist, however, with liquid level detecting techniques based on capacitance measurement. For example, the ability to detect very small changes in capacitance, that is, sensitivity, is a common problem. The sensitivity problem often leads to complex circuits connected to the sensing elements and/or complex structures associated with the sensing element or the container holding the liquid. Furthermore, liquid level detecting devices which detect a change in capacitance often utilize radio frequency (RF) signals applied or coupled to the sensing element. However, the RF signals can interfere with the operation of other devices coupled to the sensing element and can cause RF emissions unless careful shielding is used.

Thus, there is a need for a liquid level sensing system exhibiting good sensitivity yet which is relatively simple in terms of electronic circuit design and associated structure and which minimizes RF interference and emissions problems.

SUMMARY OF THE INVENTION

The present invention overcomes the limitations and drawbacks described above with known liquid level sensing devices, providing a liquid level sensing system of great sensitivity yet of relatively simple and reliable design.

In accordance with the present invention, a liquid level sensing system includes a conductive sensing probe. A reactive element is disposed on the probe. An oscillator includes a tuned circuit that is coupled to the probe so as to include the reactive element in the tuned circuit. The tuned circuit controls the frequency of the oscillator. The output of the oscillator is applied to a detector which generates a predetermined output when the detector detects a change in the output of the oscillator indicating contact between the probe and liquid caused by a change in the capacitance sensed by the probe.

The oscillator may include another element in the tuned circuit responsive to a control signal for varying the resonate frequency of the tuned circuit and thus the oscillator. The detector may also generate the control signal so as to maintain the frequency of the oscillator at some predetermined frequency. A differentiator responsive to the control signal detects a rapid change in the control signal applied to the oscillator, thus indicating contact between the probe and a liquid surface.

DETAILED DESCRIPTION

Figure 1:
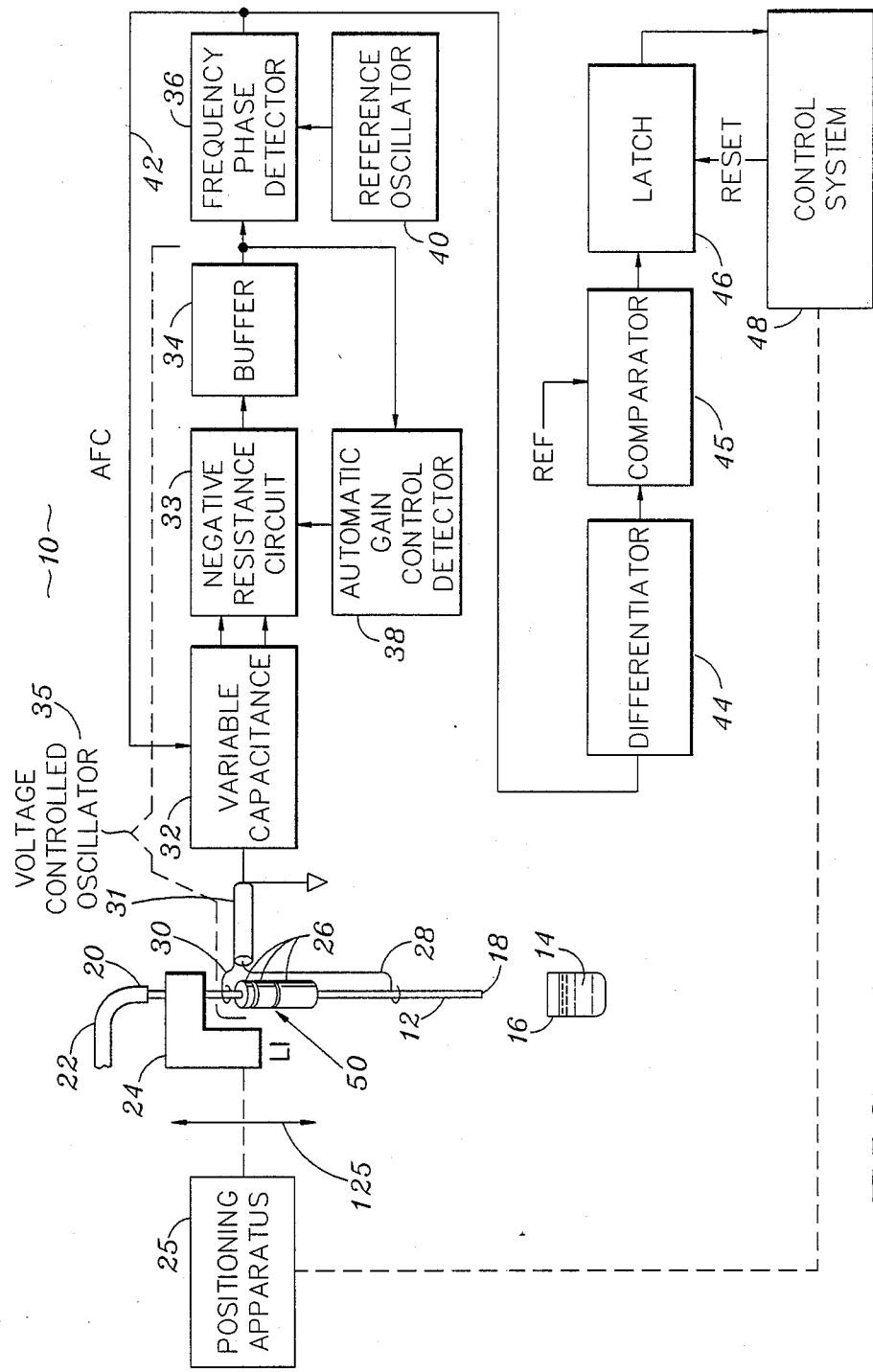
FIG. 1 is a block diagram of a liquid level sensing system in accordance with the present invention.

With reference to FIG. 1, a liquid level sensing system 10 in accordance with the present invention includes a conductive probe 12 adapted to aspirate liquid 14 held in a container 16. The probe 12 is formed of a conductive material and may take the form of a length of stainless steel hypodermic needle tube stock. A lower end 18 of the probe 12 is open and an upper end 20 is connected via a suitable conduit 22 to, for example, a syringe type precision pump for aspirating the liquid 14 into the probe 12, all in a known fashion. The probe 12 may be carried by a probe support 24 which is in turn positioned by a suitable probe positioning apparatus 25 for moving the probe 12 vertically with respect to the container 16 and horizontally for positioning the probe 12 at various locations for liquid aspiration and delivery. Such probe positioning apparatus 25 are well known in the art as many be used, for example, in automated clinical chemistry analyzers.

The probe 12 carries a plurality of ferrite beads 26. The ferrite beads 26 are fixed on the probe 12 between two conductors 28 and 30 which are each connected to the probe 12. The lower conductor 28 may take the form of a center conductor of a length of coaxial cable 31. The upper conductor 30 is connected to the shield of the cable 31, the shield of the cable 31 being in turn connected to system ground. The cable 31 is of sufficient length to accommodate the movement of the probe 12.

The center conductor of the cable 31, that is, the lower conductor 28 fixed to the probe 12, is connected to a variable capacitance 32. The variable capacitance 32, along with the reactive element being an inductance in the form of the ferrite beads 26 and a small capacitance sensed by the portion of the probe from the beads 26 to the tip 18, forms a tank circuit. The variable capacitance 32 is coupled to a negative resistance circuit 33 which serves to overcome the losses in the tank circuit. The output of the negative resistance circuit 33 is applied to a buffer 34 to isolate the circuit 33 from the following stages. Taken together, the tank circuit formed by the beads 26 and the variable capacitance 32, the negative resistance circuit 33, and the buffer 34 form a voltage controlled oscillator (VCO) 35. The frequency of the VCO 35 is determined by the resonant frequency of the tank circuit, that is, by the total capacitance and inductance present in the tank circuit.

The VCO 35 output is applied to a frequency/phase detector 36 and an automatic gain control (AGC) detector 38. The AGC detector 38 monitors the amplitude of the VCO 35 output and provides a feedback signal to the negative resistance circuit 33 to maintain the magnitude of the VCO 35 output at an essentially constant level. In the embodiment disclosed herein, the VCO 35 output is approximately 300 mV peak to peak.

A reference oscillator 40 provides a reference signal having a predetermined constant frequency to detecting means being the frequency/phase detector 36. The output of the frequency/phase detector 36 is in turn applied as an automatic frequency control (AFC) signal on line 42 to the variable capacitance 32 which exhibits an adjustable capacitance is response to the AFC signal. The adjustable capacitance 32 in the tank circuit described above adjusts the frequency of the VCO 35.

The VCO 35, frequency/phase detector 36, and reference oscillator 40, form a closed frequency control loop that constantly adjusts the VCO 35 so as to maintain a constant output frequency. More particularly, the frequency/phase detector 36 compares the frequency and phase of the reference signal from the oscillator 40 to the output of the VCO 35 and varies its output signal in a direction that tends to shift the frequency of the VCO 35 output so as to match the frequency and phase of the reference signal. The frequency/phase detector 36 compares frequency when the VCO 35 output and the reference signal are essentially unequal. If the output of th4e VCO 35 and the reference signal are essentially the same frequency, the frequency/phase detector 36 operates primarily as a phase detector, all in a fashion well known in the art.

The output of the frequency/phase detector 36 is also applied to a differentiator 44. The differentiator 44 develops an output that is proportional to the rate of change of the AFC signal developed by the frequency/phase detector 36. The differentiator 44 output is applied to a comparator 45. The comparator 45 compares the output of the differentiator 44 to a predetermined reference level. If the output of the differentiator 44 exceeds the reference level, the comparator 45 provides a pulse to a latch 46, setting the latch. The output of the latch 46 may be, for example, applied to a computer-based control system 48 which controls positioning apparatus 25 to thus control the movement of the probe 12. The control system 48 may also apply a reset signal to the latch 46 to reset the latch 46, awaiting the next pulse from the differentiator 44.

In operation, the probe 12 may be moved about by the positioning apparatus 25. As the probe 12 moves as indicated, the by arrows 125 probe 12 senses a certain capacitance through the surrounding air. This capacitance varies slowly as, for example, the probe 12 moves with respect to surrounding objects or, as a further example, objects such as operator's hands move around and near the probe 12. The slowly changing capacitance detected by the probe 12 results in changes in the probe 12 capacitance present in the tank circuit. Thus, in order to maintain the output of the VCO 35 at the frequency of the reference oscillator 40, corresponding slow compensating changes in the control signal appearing on the AFC line 42 are generated by the frequency/phase detector 36. These slow changes are differentiated by the differentiator 44. Because the changes are slow, the output of the differentiator 44 does not exceed the reference level applied to the comparator 45. Thus, no output from the comparator 45 is applied to the latch 46.

Immediately upon contact between the probe lower end 18 and the surface of the liquid 14, the capacitance sensed by the probe 12 suddenly changes. It is believed that this sudden change is due in part to a "wicking" action of the liquid 14 wetting the end 18 of the probe 12 as the end 18 breaks the surface tension of the liquid 14 surface. This sudden change in capacitance (on the order of about 0.2 pF to about 0.5 pF with a 30 ul serum sample as the liquid 14) tends to suddenly shift the resonant frequency of the tank circuit and thus the output frequency of the VCO 35. This frequency shift is detected by the frequency/phase detector 36 which changes its output signal in a direction required to adjust the variable capacitance 32 in the tank circuit so as to compensate for the capacitance change sensed by the probe 12. The output of the frequency/phase detector 36 is applied via the AFC line to the VCO 35, adjusting the tank circuit capacitance so that the output frequency and phase of the VCO 35 again matches that of the reference oscillator 40. It is to be understood that the frequency shift by the VCO 35 and the corresponding change in the output of the frequency/phase detector 36 so as to maintain the output frequency of the VCO 35 at the same frequency as the reference oscillator 40 is very rapid. In the embodiment disclosed herein, the change occurs in less than about 1 msec. This rapid change is differentiated by the differentiator 44, producing a corresponding output that exceeds the reference level applied to the comparator 45. The comparator 45 in turn generates an output pulse that is applied to the latch 46. The output of the latch is applied to the control system 48, indicating that the lower end of the probe 12 has contacted the surface of the liquid 14.

Thus, a system 10 in accordance with the present invention utilizes the rate of change of a frequency control signal applied to a voltage-controlled oscillator to detect contact between the probe 12 and the liquid 14. The probe 12 provides a portion of the capacitance present in the tank circuit which controls the frequency of the VCO 35 such that the VCO 35 output frequency is responsive to changes in the capacitance sensed by the probe 12. The system 10 is relatively insensitive to noise and stray capacitance.

The ferrite beads 26 also isolate the lower portion of the probe 12 from the upper portion of the probe 12 and the fluid contained within the conduit 22. This isolation helps prevent unwanted RF radiation and isolates the lower portion of the probe 12 from interference which might otherwise be conducted down the conduit 22. The isolation also helps prevent unwanted triggering of the apparatus 10 by, for example, touching the conduit 22. The signal that appears on the probe 12 is essentially a clean sine wave free of harmonics, also helping to control RF interference. Furthermore, the short probe 12 length makes a poor antenna at the frequency of the signal appearing on the probe which in the embodiment disclosed herein is about 6 MHz. The probe 12 may be insulated such as by coating with Teflon or may be uninsulated.

Figure 2:
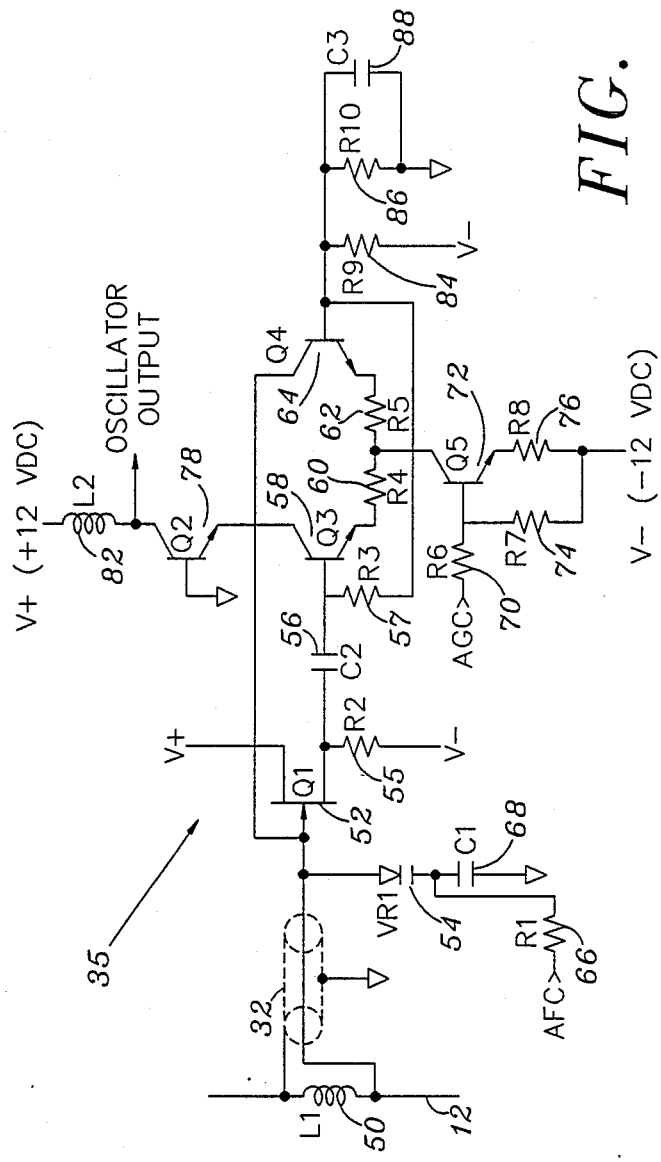
FIG. 2 is a schematic diagram of a voltage controlled oscillator useful in the system of FIG. 1.

With reference now to FIG. 2, the VCO 35 of FIG. 1 is illustrated in detail. An inductor L1 indicated by 50 formed numeral by the ferrite beads 26 on the probe 12 is connected via the coaxial cable 31 to the gate of a field effect transistor (FET) 52. The center conductor of the cable 31 is also connected to the anode of a varactor 54 which, together with the impedance 50, forms a resonant tank circuit for the VCO 35. The FET 52 forms a high impedance buffer driver coupled via resistors 55 and 57 and a capacitor 56 to the base of a transistor 58 connected in a common collector configuration. The emitter of the transistor 58 is connected through emitter resistors 60 and 62 to a transistor 64 connected in a common base configuration. The collector of the transistor 64 is connected to the node formed by the center conductor of the cable 31, the gate of the FET 52 and anode of the varactor 54. The FET 52 and the transistors 58 and 64 together form the negative resistance circuit 33 of FIG. 1. The base of the transistor 64 is connected to the V− supply via a resistor 84 and to ground via a parallel connected resistor 86 and capacitor 88.

The cathode of the varactor 54 is connected via a resistor 66 to the AFC signal developed by the frequency/phase detector 36 (FIG. 1). A capacitor 68 couples the resistor 66 and the varactor 54 cathode to ground.

The signal from the AGC detector 38 is applied through a resistor 70 to the base of a constant current source transistor 72. The base and emitter of the transistor 72 are connected to the V− supply via resistors 74 and 76, respectively. The collector of the transistor 72 is connected between the resistors 60 and 62, providing a constant current source for the transistors 58 and 64. The collector of a grounded base transistor 78 is connected to the V+ supply via an RF choke inductor 82. The emitter of the transistor 78 is connected to the collector of the transistor 58. The transistor 78 operates in a cascade mode and forms the buffer 34 of FIG. 1.

Sample values for the components shown in FIG. 2 are are follows:

TABLE 1

| L1 | ≈1.5 μH |
|---|---|
| L2 | 10 μH |
| VR1 | MVAM115 |
| Q1 | 2N5485 |
| Q2 | 2N2222 |
| Q3 | 2N2222 |
| Q4 | 2N2222 |
| Q5 | 2N2222 |
| C1 | 0.01 μF |
| C2 | 0.01 μF |
| C3 | 0.01 μF |
| R1 | 1K |
| R2 | 1K |
| R3 | 2.2K |
| R4 | 20 |
| R5 | 20 |
| R6 | 3.6K |
| R7 | 1K |
| R8 | 100 |
| R9 | 2.2K |
| R10 | 1.6K |

With reference to FIGS. 1 and 2, as the probe 12 contacts the surface of the liquid 14, the capacitance sensed by the probe abruptly changes. The change in capacitance changes the resonant frequency of the tank circuit. The VCO 35 accordingly shift frequency in response to this change in the resonant frequency of the tank circuit. The AFC signal, developed as described above, is applied to the varactor 54. The polarity and magnitude of the change in the AFC signal is sufficient to adjust the capacitance of the varactor 54 so as to compensate for the change in capacitance sensed by the probe 12.

The output of the AGC detector 38 is applied through the resistor 70 to the constant current source transistor 72, varying the amount of current conducted by the transistor 72. The AGC adjustment applied to the transistor 72 maintains the output of the oscillator derived at the collector of the transistor 78 essentially constant with the VCO 35 operating in a linear range and the output thereof essentially a pure sine wave signal.

The VCO 35 generates a relatively pure sine wave output signal free of harmonic radiation and thus attendant radio frequency interference. Because the frequency and magnitude of the VCO 35 output remains essentially constant, the VCO 35 within the system 10 eliminates unpredictable results which might otherwise occur in a system utilizing a free running oscillator which could interfere with the operation of, for example, the control system 48 or generate radio frequency interference problems.

Thus, the system 10 in accordance with the present invention provides sensitive and repeatable liquid level sensing utilizing a single probe not otherwise known in or suggested by the art.

The present invention is know to be limited by the detailed description set forth hereinabove but is to be afforded the full range of the appended claims and all equivalence thereto.

What is claimed is:

1. A liquid level sensing apparatus comprising:
   a conductive sensing member;
   a reactive element disposed on the member;
   oscillator means having an output and a tuned circuit including at least a portion of the member and the reactive element, the tuned circuit controlling the frequency of the oscillator means output; and
   detecting means responsive to the output of the oscillator means for detecting the oscillator means output frequency and generating a predetermined output when the detecting means detects a shift in the oscillator means output frequency indicating contact between the member and a liquid.

2. Apparatus as in claim 1 wherein the detecting means further includes means for generating a frequency control signal which varies with the frequency of the oscillator means output as compared to a signal from a reference signal generator, and the oscillator means includes means for varying an element of the tuned circuit in response to the frequency control signal to adjust the oscillator means output frequency.

3. Apparatus as in claim 2 wherein the detecting means further includes means for differentiating the frequency control signal and generating an output when a rate of change of the frequency control signal indicates initial contact between the conductive sensing member and the surface of a liquid.

4. A liquid level sensing apparatus comprising:
   a conductive probe adapted to aspirate liquid;
   a reactive element disposed on the probe;
   oscillator means having an output and a tuned circuit including at least a portion of the probe and the reactive element, the tuned circuit controlling the frequency of the oscillator means output, the oscillator means further including means for varying an element of the tuned circuit in response to a frequency control signal to adjust the oscillator means output frequency;
   a reference signal generator generating an output having a predetermined fixed frequency;
   detecting means responsive to the output of the oscillator means and the reference signal generator for generating a frequency control signal which varies with the frequency of the oscillator means output as compared to the signal from the reference signal generator; and differentiating means responsive to the frequency control signal for differentiating the frequency control signal and generating an output when the rate of change of the frequency control signal indicates initial contact between the probe and the surface of a liquid.

5. A liquid level sensing apparatus comprising:
a conductive sensing probe;
a reactive element disposed on the probe;
oscillator means having an output and a tuned circuit including at least a portion of the probe and the reactive element, the tuned circuit controlling the frequency of the oscillator means output; and
detecting means responsive to the output of the oscillator means for detecting the oscillator means output frequency and generating a predetermined output when the detecting means detects a shift in the oscillator means output frequency indicating contact between the probe and a liquid.

6. Apparatus as in claim 5 wherein the detecting means further includes means for generating a frequency control signal and the oscillator means includes means for varying an element of the tuned circuit in response to the frequency control signal to control the oscillator means output frequency.

7. Apparatus as in claim 6 wherein the detecting means further includes means for differentiating the frequency control signal and for generating an output when a rate of change of the frequency control signal indicates initial contact between the conductive sensing member and the surface of a liquid.

8. Apparatus as in claim 7 including means for generating a reference frequency signal and wherein the frequency control signal is responsive to variations between the frequency of the oscillator means output and the reference frequency signal.

9. Apparatus as in claim 6 wherein the element for varying is a variable capacitor.

10. Apparatus as in claim 5 wherein the probe includes a passage for liquid.

11. Apparatus as in claim 5 wherein the reactive element includes a plurality of conductive beads.

12. A liquid level sensing apparatus comprising:
a conductive probe;
a reactive element disposed on the probe;
oscillator means having an output and a tuned circuit including at least a portion of the probe and the reactive element, the tuned circuit controlling the frequency of the oscillator means output, the oscillator means further including means for varying an element of the tuned circuit in response to a frequency control signal to control the oscillator means output frequency;
a reference signal generator generating an output having a predetermined fixed frequency;
detecting means responsive to the output of the oscillator means and the reference signal generator for generating a frequency control signal which varies in response to the frequency of the oscillator means output as compared to the signal from the reference signal enervator; and
differentiating means responsive to the frequency control signal for differentiating the frequency control signal and generating an output when the rate of change of the frequency control signal indicates initial contact between the probe and the surface of a liquid.

13. A liquid level sensing apparatus comprising:
a conductive sensing member;
a reactive element disposed on the member;
oscillator means having an output and a tuned circuit including at least a portion of the member and the reactive element, the tuned circuit controlling the frequency of the oscillator means output; and
detecting means responsive to the output of the oscillator means for detecting the oscillator means output frequency and generating a predetermined output when the detecting means detects a shift in the oscillator means output frequency indicating contact between the member and a liquid, the frequency shift being detected in a non-radio frequency range.

14. Apparatus as in claim 13 wherein the detecting means further includes means for generating a frequency control signal, and the oscillator means includes means for varying an element of the tuned circuit in response to the frequency control signal to control the oscillator means output frequency.

15. A liquid level sensing apparatus comprising:
a conductive sensing member;
a reactive element disposed on the member;
oscillator means having an output and a tuned circuit including at least a portion of the member and the reactive element, the tuned circuit controlling the frequency of the oscillator means output; and
detecting means responsive to the output of the oscillator means for detecting the oscillator means output frequency and generating a predetermined output when the detecting means detects a shift in the oscillator means output frequency indicating contact between the member and a liquid wherein the detecting means further includes means for generating a frequency control signal which varies with the frequency of the oscillator means output as compared to a signal from a reference signal generator, and the oscillator means includes means for varying an element of the tuned circuit in response to the frequency control signal to adjust the oscillator means output frequency, and
wherein the detecting means further includes means for differentiating the frequency control signal and generating an output when a rate of change of the frequency control signal indicates initial contact between the conductive sensing member and the surface of a liquid.

16. A liquid level sensing apparatus comprising:
a conductive sensing probe;
a reactive element disposed on the probe;
oscillator means having an output and a tuned circuit including at least a portion of the probe and the reactive element, the tuned circuit controlling the frequency of the oscillator means output; and
detecting means responsive to the output of the oscillator means for detecting the oscillator means output frequency and generating a predetermined output when the detecting means detects a shift in the oscillator means output frequency indicating contact between the probe and a liquid, wherein the detecting means further includes means for generating a frequency control signal and the oscillator means includes means for varying an element of the tuned circuit in response to the frequency control signal to control the oscillator means output frequency, and wherein the detecting means further includes means for differentiating the frequency control signal and for generating an output when a rate of change of the frequency control signal indicates initial contact between the conductive sensing member and the surface of a liquid.

17. Apparatus as in claim 16 including means for generating a reference frequency signal and wherein the frequency control signal is responsive to variations between the frequency of the oscillator means output and the reference frequency signal.

18. Apparatus as in claim 16 wherein the element for varying is a variable capacitor.

19. A liquid level sensing apparatus comprising:
a conductive sensing probe;
a reactive element including a plurality of conductive beads disposed on the probe;
oscillator means having an output and a tuned circuit including at least a portion of the probe and the reactive element, the tuned circuit controlling the frequency of the oscillator means output; and
detecting means responsive to the output of the oscillator means for detecting the oscillator means output frequency and generating a predetermined output when the detecting means detects a shift in the oscillator means output frequency indicating contact between the probe and a liquid.

20. Apparatus as in claim 19 wherein the detecting means further includes means for generating a frequency control signal and the oscillator means includes means for varying an element of the tuned circuit in response to the frequency control signal to control the oscillator means output frequency.

21. Apparatus as in claim 20 wherein the detecting means further includes means for differentiating the frequency control signal and for generating an output when a rate of change of the frequency control signal indicates initial contact between the conductive sensing member and the surface of a liquid.

22. Apparatus as in claim 21 including means for generating a reference frequency signal and wherein the frequency control signal is responsive to variations between the frequency of the oscillator means output and the reference frequency signal.

23. Apparatus as in claim 20 wherein the element for varying is a variable capacitor.

* * * * *

UNITED STATES PATENT AND TRADEMARK OFFICE
CERTIFICATE OF CORRECTION

PATENT NO. : 4,912,976

DATED : April 3, 1990

INVENTOR(S) : Labriola

It is certified that error appears in the above-identified patent and that said Letters Patent is hereby corrected as shown below:

Column 2, line 36 reads:

...as many be used...

should read:

...as may be used...

Column 3, line 27 reads:

...th4e...

should read:

...the...

UNITED STATES PATENT AND TRADEMARK OFFICE
CERTIFICATE OF CORRECTION

PATENT NO. : 4,912,976

DATED : April 3, 1990

INVENTOR(S) : Labriola

It is certified that error appears in the above-identified patent and that said Letters Patent is hereby corrected as shown below:

Column 3, line 49 reads:

...indicated, the by arrows 125 probe 12...

should read:

...indicated by arrows 125, the probe 12...

Column 4, line 60 reads:

...by 50 formed numeral...

should read:

...by numeral 50 formed...

Signed and Sealed this

Nineteenth Day of November, 1991

*Attest:*

HARRY F. MANBECK, JR.

*Attesting Officer*    *Commissioner of Patents and Trademarks*